United States Patent [19]

Emblem et al.

[11] 4,211,717
[45] Jul. 8, 1980

[54] MANUFACTURE OF ALKYL SILICATES

[75] Inventors: Harold G. Emblem, Mirfield; Anup K. Das, Bromley; Kenneth Jones, Tyldesley, all of England

[73] Assignee: Zirconal Processes Limited, Bromley, England

[21] Appl. No.: 23,243

[22] Filed: Mar. 23, 1979

[51] Int. Cl.$^2$ ............................................. C07F 7/04
[52] U.S. Cl. ................................................... 556/470
[58] Field of Search ................................. 260/448.8 A

[56] References Cited

U.S. PATENT DOCUMENTS

| | | | |
|---|---|---|---|
| 2,445,576 | 7/1948 | Haber | 260/448.8 A |
| 2,569,784 | 10/1951 | Smith | 260/448.8 A |
| 3,232,972 | 2/1966 | Beanland | 260/448.8 A |
| 3,627,807 | 12/1971 | Bleh et al. | 260/448.8 A |
| 3,641,077 | 2/1972 | Rochow | 260/448.8 A X |
| 3,775,457 | 11/1973 | Muraoka et al. | 260/448.8 A X |

*Primary Examiner*—Paul F. Shaver
*Attorney, Agent, or Firm*—Christensen, O'Connor, Johnson & Kindness

[57] ABSTRACT

Ethyl or other lower alkyl silicate is prepared by the direct reaction of alcohol and silicon thereby avoiding the generation of hydrogen chloride as a by-product. The reaction is carried out at elevated temperature in a catalytic solution of high thermal capacity.

20 Claims, No Drawings

MANUFACTURE OF ALKYL SILICATES

DESCRIPTION

This invention relates to the manufacture of alkyl silicates more particularly ethyl silicate. Ethyl silicate finds industrial application as ethyl orthosilicate, tetraethoxysilane as ethyl polysilicate, ethoxypolysiloxanes, also as a mixture of ethyl orthosilicate and ethyl polysilicates. The most readily commercially available product is "technical" ethyl silicate which is a mixture of ethyl orthosilicate and ethyl polysilicates and contains silicon equivalent to a silica content of approximately 40%. Amongst the important industrial application of ethyl silicate is the binding of refractory powders. Ethyl silicate when hydrolysed forms a hydrolysate which is gellable, usually with the aid of a catalyst, to provide a rigid and coherent gel. Slurries of refractory powder and the gellable hydrolysate can thus be formed to the desired shape either by cavity or pattern moulding and thereafter set in this shape by gelling of the hydrolysate.

The most widely used method for the preparation of ethyl silicate is the reaction of silicon tetrachloride with ethyl alcohol. This process has the disadvantage that hydrogen chloride is obtained as a by-product which has to be removed and thereafter disposed of. The removal of hydrogen chloride requires expensive equipment and detracts from the economy of the manufacturing method and the disposal of hydrogen chloride which constitutes a hazardous waste is an expensive and environmentally undesirable operation.

It is an object of the present invention to provide a method for the manufacture of ethyl silicate which is based on the direct reaction of ethanol with silicon or silicides, i.e. compounds of metallic elements with silicon. Although the reactions of the present invention will be described with primary reference to ethanol it should be recognised that they are in principle applicable to other alcohols. The reaction between ethanol and silicon which produces ethyl silicate and hydrogen gas is, in principle, known but has not been effectively commercialised due to difficulties in obtaining economic yields.

According to the present invention the reaction between ethanol and silicon or a silicide is carried out at a high temperature in a catalytic solution which has sufficient thermal capacity effectively to maintain the temperature and to catalyse the reaction and to discharge tetraethoxysilane as a vapour together with ethanol vapour and hydrogen gas. The thermal capacity of the catalytic solution can be maintained and indeed increased by stepwise additions of ethanol and silicon or a silicide, then tetraethoxysilane and ethanol are removed as vapour and the sequence repeated.

The reaction can be summarised as follows:

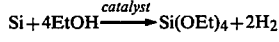

The invention is based on the recognition that although the reaction between silicon and ethanol is an exothermic reaction the discharge of the vapour products, i.e. the mixture of ethanol and tetraethoxysilane vapours draws from the reaction their latent heat of vapourisation. Also the addition of the reagents can lower the temperature of the system. In order to maintain the high temperature necessary for economic realisation of the reaction there has to be sufficient thermal capacity in the catalytic solution to maintain this in spite of the heat withdrawn by the vapourisation of the products. It is necessary for the reagents to have sufficient dwell time in the solution for the reaction to take place.

The necessary thermal capacity can be achieved (a) by carrying out the reaction at as high a temperature as is practicable. This should at least be at the boiling point of the tetraethoxysilane/ethanol mixture. Thus a reaction of temperature of at least 100° C. and possibly as high as 180° C. is envisaged. 135°–170° C. is the broad preferred range and 150°–165° C. the narrower preferred range.

(b) by maintaining a relatively large volume of catalytic solution. Thus there should be at least 500 ml of catalytic solution for each mole of silicon. The upper limit of the catalytic solution/silicon ratio is not so important but 3000 ml/mole is a reasonable figure.

(c) by the selection of an appropriate catalytic solution as will be described.

The reaction may be carried out using batches of reagents or may be started using batches of reagents and then maintained by continuous addition of ethanol and silicon or silicide to a relatively large volume of the catalytic solution. A preferred expedient is to introduce the reagents below the surface of the solution preferably near the bottom of the reaction vessel. When the reagents are not preheated, on entry they initially lower the temperature of the solution and then commence their catalysed reaction. As the reagents rise through the catalytic solution the reaction proceeds until the mixture of ethanol and products is vapourised with a considerable loss of heat. The large thermal capacity of the volume of the catalytic solution at elevated temperature readily provides that heat. The rate of reaction can be monitored by measuring the rate of evolution of hydrogen.

The action of the catalyst in this particular reaction is to form a complex with the reagents, the complex thereafter disassociating, regenerating the catalyst and the reaction products.

In principle therefore industrial catalysts which operate in this manner can be used and of such the metal alkoxides are preferred. The solvent for the catalyst must not undergo an irreversible reaction with the catalyst under the relatively extreme reaction conditions and must be able to survive these conditions. The solvent must therefore have a high boiling point and be chemically inert and neutral.

Preferred solvents are linear oligomers of the following general formula I:

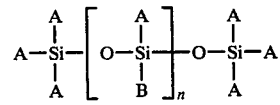

where n is 1 or a whole number greater than 1 or cyclic compounds of the general formula II:

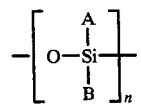

where n is 3 or a whole number greater than 3 A is $CH_3$, OR where R is $C_1$–$C_4$ alkyl preferably ethyl, O($CH_2$C-

$H_2O)_mD$, where D is methyl, ethyl or phenyl and m is 1 or 2. Preferably m is 1 and D is ethyl. Preferably all the A groups are the same in each compound. B is the same as A and when A is $CH_3$, B can also be $C_6H_5$. When A is OR or $O(CH_2CH_2O)_mD$, the solvent may also contain $SiA_4$ and/or $A_3Si-O-SiA_3$ species, provided that there is not more than 20% by weight of $SiA_4$ and 40% by weight of $A_3Si-O-SiA_3$. When A is $CH_3$, the solvent may also contain not more than 20% by weight of $Si(OR)_4$ and/or $Si[O(CH_2CH_2O)_mD]_4$ species. When A is $CH_3$ and B is $C_6H_5$ the solvent may also contain not more than 60% of $Si(OR)_4$ species, R being preferably ethyl.

The solvent may also comprise a mixture of components having different A groups and it may also be a mixture of cyclic and linear polymers.

Examples of suitable solvents are the methyl polysiloxanes and the methyl phenyl polysiloxanes, which may be linear or cyclic, also the ethoxypolysiloxanes. Tetraethoxysilane and technical ethyl silicate are other suitable solvents one example of the latter is described in British Pat. No. 674,137. It is important that the reagents should be as dry and pure as possible. Specifically the alcohol should be dried using a molecular sieve.

The preferred metal alkoxides are the alkali metal alkoxides particularly those of sodium and potassium. A mixture of sodium alkoxide and potassium alkoxide is advantageous. The alkali metal alkoxide is preferably derived from ethanol or the alcohol $HO(CH_2CH_2O)_mD$. Another possible catalyst is the reaction product of sodium ethoxide and 2-ethoxyethanol.

According to a more restricted aspect the present invention provides a method of preparing tetraethoxysilane which comprises preparing the catalytic solution for example by the following steps.

(1) Dissolving a metal or metals in an alcohol under an inert atmosphere, for example nitrogen. When more than one metal is used they will preferably be added sequentially.

(2) Warming the solution produced in (1) preferably under reflux. The warming time should be at least 1.5 hours preferably at least 4 hours.

(3) Adding to the metal alkoxide catalyst produced a relatively large volume of high boiling point inert and neutral solvent.

(4) Adding to the catalytic solution silicon or a silicide in admixture with liquid dry ethanol.

(5) Warming the solution preferably to at least 110° C. to initiate the catalysed reaction; and (6) Adding further dry liquid ethanol.

Steps (4) to (6) can be modified by adding the silicon or metal silicide to the solution of (3), subsequently warming and thereafter adding the ethanol.

For industrial application steps (1) to (3) can be carried out as a separate process. The ethanol can be introduced as a vapour into the lower part of the reaction vessel.

The reaction which may be carried out continuously by addition of ethanol and silicon or metal silicide produces a mixture of ethanol and tetraethoxysilane vapours which is distilled off.

All steps are preferably carried out under an inert atmosphere as is mandatory for step (1).

The product of the process described above is tetraethoxysilane and the present invention also proposes converting the tetraethoxysilane to technical ethyl silicate by controlled hydrolysis and condensation-polymerisation thereby increasing the silica equivalent.

The preferred technical ethyl silicate contains silicon equivalent to approximately 40% $SiO_2$ by weight.

The following description of particular embodiments and numbered examples illustrate the invention:

A—Metal alkoxide preparation

All preparations are carried out in an atmosphere of dry nitrogen.

METHOD 1

2-Ethoxyethanol (290 ml, 2.96 mole) was introduced into a flask fitted with a reflux condenser and nitrogen inlet. The vessel was flushed with nitrogen and potassium (19 g, 0.5 mole) was slowly added over a 3 hour period, followed by sodium (11.5 g, 0.5 mole). The mixture was refluxed for 4 hours until hydrogen evolution ceased. The initial solution was pale yellow but turned deep red after 2 hours.

METHOD 2

Using the apparatus and procedure of Method 1, to 2-ethoxyethanol (180 ml, 1.76 mole) sodium (5.58, 0.254 mole) was slowly added, followed by potassium (9.42 g, 0.242 mole) and the resulting mixture refluxed for two hours.

METHOD 3

Sodium (7.4 g, 0.311 mole) was slowly added to 2-ethoxyethanol (170 ml, 1.75 mole) and the resulting mixture refluxed for 1 hour. In a separate vessel, potassium (13 g, 0.33 mole) was slowly added to 2-ethoxyethanol (160 ml, 1.65 mole) and the resulting mixture refluxed for 1 hour. The two solutions may be combined for use, or used individually.

METHOD 4

Toluene (40–50 ml) was placed in a flask fitted with a reflux condenser, nitrogen inlet and dropping funnel, whose lower end was under the toluene. The flask was flushed with dry nitrogen which was passed through th flask throughout the course of the reaction. Potassium (19 g, 0.5 mole) was added, then 2-ethoxyethanol (160 ml, 1.7 mole) was slowly added dropwise. When the potassium had reacted, sodium (11.5 g, 0.5 mole) was added, then further 2-ethoxyethanol added dropwise until a total volume of 300 ml was added. The solution was warmed and toluene distilled off at 121° C. The remaining solution was refluxed for 4 hours. The 2-ethoxyethanol can also be added to sodium and potassium metals concurrently.

METHOD 5

Using the apparatus and procedure of Method 1, dry ethanol (100 ml, 1.77 mole) was used to dissolve sodium (4.75 g, 0.207 mole) and potassium (9.29 g, 0.238 mole) which were slowly added in the order given. The mixture was refluxed for two hours, then used immediately. Sodium and potassium may be dissolved in ethanol individually.

METHOD 6

A 2 liter, 5 necked flask, fitted with a partial take-off head, mechanical stirrer, dropping funnel, thermometer and nitrogen inlet was flushed with nitrogen after introducing a solution comprising technical ethyl silicate (40% $SiO_2$ w/w–110 ml) and dry ethanol (46 g–1 mole). To this solution was added potassium (5.5 g, 0.14 mole), then sodium (3.2 g, 0.16 mole). The mixture was warmed for 3 hours to give the catalytic solution.

METHOD 7

Using the procedure of Method 1, methyldigol (200 ml, 1.70 mole) was used as solvent for sodium (5.67, 0.247 mole), then for potassium (9.65 g, 0.247 mole).

METHOD 8

Using the procedure of Method 1, 2-phenoxyethanol (250 ml, 1.99 mole) was used as solvent for sodium (5.66 g, 0.246 mole) and for potassium (9.82 g, 0.252 mole).

METHOD 9

Using a flask fitted with a reflux condenser and dropping funnel, sodium ethoxide solid (Na OEt.2EtOH, 83.6 g, 0.54 mole) was dissolved in 2-ethoxyethanol (250 ml, 2.58 mole), which was added dropwise over a period of 2 hours. There was a very exothermic reaction, giving a liquid mixture. The dropping funnel and reflux condenser were removed and replaced by a distillation head and condenser. The mixture was heated under reduced pressure (100 mm) and 102 grams distillate collected over 2 hours. This distillate comprised ethanol 41 parts and 2-ethoxyethanol 59 parts. The residue was used in the preparation of tetraethoxysilane.

B—Production of tetraethoxysilane.

EXAMPLE 1

A 2 liter, 5 necked flask fitted with a partial take-off head, mechanical stirrer, dropping funnel and nitrogen gas inlet was flushed with nitrogen. Then 170 ml of metal alkoxide solution prepared as described in Method 2 was added, together with 340 ml of tetraethoxysilane to form the catalytic solution. 14 g of silicon powder, average particle size 50–80 microns, composition 97% Si, 3% Fe, were added, i.e. 510 ml catalytic solution/mole silicon. Then 30 ml dry ethanol were added. The ethanol must be dried prior to use either by treatment with a molecular sieve (e.g. Linde type 3A) or by distillation over sodium or magnesium. The mixture was heated by an electric heating mantle. When the reactor temperature reached 120° C., the distillation head temperature rose to 90° C. After 80 ml distillate (impure tetraethoxysilane) was collected, the distillation head temperature fell to ambient and the reactor temperature rose to 150° C., at which temperature it was maintained for the remainder of the reaction period. The reaction was monitored by measuring the rate of hydrogen solution. Further reactants were added when the rate fell to less than 30 ml/min. Silicon was added in batches of 7 or 14 grams, ethanol (dry) being added dropwise at a rate such that the reactor temperature remained at 150° C. The reaction was run in this way for 26 hours. A total of 70 g (2.14 mole) silicon was added, 93% being converted to tetraethoxysilane. The average rate of production of tetraethoxysilane was 18 g/hour. The final reaction mixture was distilled at atmospheric pressure to recover pure tetraethoxysilane.

EXAMPLE 2

180 ml of metal alkoxide solution prepared by Method 1 was added to 500 ml of technical ethyl silicate to form the catalytic solution. To this was added 12 grams of silicon (i.e. 1587 ml catalytic solution/mole silicon) and 303.5 grams (6.6 mole) dry ethanol. The mixture was heated for 3 hours at 70°–80° C. then the temperature was raised to 120° C., 580 ml of distillate (b. 82°–90° C.) being collected. The temperature was raised to 145° C. and a 4:1 molar ratio slurry of ethanol:silicon added. The reaction temperature rose and was maintained in the temperature range 165°–190° C. by adjusting the rate of addition of the slurry. Distillate (b. 115°–130° C.) was collected at the rate of about 90 ml/hour during the 40 hours which the reaction was run, a total of 3500 ml being collected. Fractionation at atmospheric pressure gave 750 g pure tetraethoxysilane b. 168°–170° C. The purity was confirmed by the IR spectrum.

EXAMPLE 3

To the catalytic solution prepared in Method 6, silicon (6 g, 798 ml catalytic solution/mole silicon) was added. Excess ethanol was distilled off until the reactor temperature reached 145° C., then a slurry of ethanol/silicon (molar ratio 4:1) was added. The reactor temperature rose to 165° C. and was maintained in the range 165°–190° C. by adjusting the rate of addition of the ethanol/silicon slurry. The reaction was carried out for 5 hours, during which time 225 ml of distillate (b. 130°–156° C.) was collected. Fractionation of this mixture gave 125 g pure tetraethoxysilane. The purity was confirmed by the IR spectrum.

EXAMPLE 4

To the metal alkoxide solution prepared as in Method 5 was added 450 ml of the tetraethoxysilane product of example 2 to give the catalytic solution. Then 14 g silicon powder, average particle size 50–60 microns, were added, i.e. 1100 ml catalytic solution/mole silicon. Following the procedure of example 1, 56 g (2.0 mole) silicon and 425 ml (7.5 mole) dry ethanol were added over a period of 22½ hours, the reactor temperature being maintained between 150°–160° C. The percentage conversion of silicon to tetraethoxysilane was greater than 95% and the production rate was 20.5 grams/hour. The product was recovered as described in example 1.

EXAMPLE 5

To 170 ml of the metal alkoxide solution prepared as described in Method 7, 340 ml of tetraethoxysilane were added to prepare the catalytic solution. To this was added 16 grams of silicon powder, average particle size 50–60 microns, i.e. 893 ml catalytic solution/mole silicon, then 30 ml dry ethanol. The mixture was heated to 150° C. and maintained in the temperature range 150°–160° C. during 23¼ hours, in which time 44 g (1.7 mole) silicon and 330 ml (5.85 mole) dry ethanol were added. The percentage conversion of silicon to tetraethoxysilane was greater than 95% and the production rate was 16.1 grams/hour.

EXAMPLE 6

To 250 ml of the metal alkoxide solution prepared as described in Method 8, 340 ml of tetraethoxysilane were added to prepare the catalytic solution. To this was added 16 grams of silicon powder, average particle size 50–60 microns, i.e. 1033 ml catalytic solution/mole silicon, then 30 ml dry ethanol. The mixture was heated as described in example 1 and maintained at a temperature of 150°–190° C. during 13½ hours. In this time 18 g (0.64 mole) of silicon and 130 ml (2.3 mole) dry ethanol were added. The percentage conversion of silicon to tetraethoxysilane was 66% and the production rate was 6.5 grams/hour.

EXAMPLE 7

To 350 ml of metal alkoxide solution prepared as described in Method 1 was added 500 ml technical ethyl silicate to prepare the catalytic solution. Then 21 g of ferrosilicon powder, average particle size 50-60 microns was added, i.e. 850 ml catalytic solution/mole silicon, together with 50 ml dry ethanol. Following the procedure of example 1, a further 72.5 g ferrosilicon (2.5 mole) and 46.2 ml dry ethanol (12.6 mole) were added over 50 hours, the temperature being maintained at 160°-180° C. The percentage conversion of silicon to tetraethoxysilane was greater than 95% and the production rate was 10 grams/hour.

EXAMPLE 8

To 290 ml of metal alkoxide solution prepared as described in Method 1 was added 700 ml tetraethoxysilane prepared as described in Example 1, to give the catalytic solution. 21 grams (1 mole Si) of ferrosilicon, average particle size 50-60 microns were added, i.e. 990 ml catalytic solution/mole silicon, together with 50 ml dry ethanol. Following the procedure of example 1, the reaction was carried out for 34 hours at an average temperature of 148° C. The percentage conversion of silicon to tetraethoxysilane was greater than 95% and the production rate was 34 grams/hour.

EXAMPLE 9

A catalytic solution was prepared by mixing 150 ml of a metal alkoxide solution prepared according to Method 1 with 250 ml of a polymethylphenyl siloxane (Dow Corning 550 fluid). 7 grams (0.25 mole) of silicon, average particle size 50-60 microns, were added, i.e. 1600 ml catalytic solution/mole silicon. Dry ethanol (50 ml) was added and the mixture was gently warmed, being maintained between 90° C. and 130° C. during the reaction (10 hours). Tetraethoxysilane was produced at rates between 11 and 56 gram/hour, depending on the reaction temperature.

EXAMPLE 10

A catalytic solution was prepared by mixing 150 ml of a metal alkoxide solution prepared according to Method 1 with 1.25 ml of a polymethylphenyl siloxane (Dow Corning 550 fluid) and with 125 ml tetraethoxysilane. 7 grams (0.25 mole) of silicon, average particle size 50-60 microns, were added, i.e. 1600 ml catalytic solution/mole silicon. Dry ethanol (50 ml) was added and the mixture was gently warmed, being maintained between 90° C. and 130° C. during the reaction (10 hours). Tetraethoxysilane was produced at rates between 11 and 112 grams/hour, depending on the reaction temperature.

EXAMPLE 11

In the preceding examples, the volume ratio of solvent to metal alkoxide solution, giving the catalytic solution is 2:1 or greater. In this example, the catalytic solution used has a volume ratio of solvent to metal alkoxide solution of 1:2.

The procedure followed is as described in example 1. The metal alkoxide solution is prepared as described in Method 1. The catalytic solution is made by adding to 350 ml of metal alkoxide solution, prepared as described in Method 1, 170 ml of tetraethoxysilane prepared as described in example 1. To this catalytic solution is added 14 g (0.5 mole) silicon powder, average particle size 50-60 microns, i.e. 1040 ml catalytic solution/mole silicon, together with 30 ml dry ethanol. The mixture was heated to 150° C. and the reaction was carried out for 14¼ hours. During this time 43.75 grams (1.75 mole) silicon and 410 ml (7.27 mole) dry ethanol were added. The percentage conversion of silicon to tetraethoxysilane was greater than 95% and the production rate was 34 grams/hour.

EXAMPLE 12

A catalytic solution was prepared by adding 350 ml of tetraethoxysilane to 175 ml of metal alkoxide solution prepared as described in Method 1. To this catalytic solution is added 14 g (0.5 mole) silicon powder, particle size 5 microns or less, i.e. 1050 ml catalytic solution/mole silicon, together with 30 ml dry ethanol. The reaction was carried out as described in Example 1, except that the dry ethanol used contained 2% v/v toluene. During 19½ hours 61 g (2.1 mole) silicon and 450 ml (9.27 mole) ethanol were added. The percentage conversion of silicon to tetraethoxysilane was greater than 95% and the production rate was 44 grams/hour.

EXAMPLE 13

Tetraethoxysilane was prepared following the procedure of example 1, except that ethanol was introduced into the reactor as a 70:30 mixture by volume of ethanol and tetraethoxysilane.

The catalytic solution was prepared by adding 350 ml of tetraethoxysilane prepared as described in example 1 to 190 ml of metal alkoxide solution prepared as described in Method 1. To this catalytic solution was added 14 grams (0.5 mole) silicon powder, particle size 5 microns or less, i.e. 1080 ml catalytic solution/mole silicon, together with 30 ml dry ethanol. The average reaction temperature was 137° C. over a 15 hour reaction period. 43.5 g (1.5 mole) silicon and 275 ml (5.88 mole) dry ethanol (as the ethanol-tetraethoxysilane mixture) were added. The percentage conversion of silicon to tetraethoxysilane was greater than 95% and the production rate was 23.6 grams/hour.

EXAMPLE 14

A catalytic solution was prepared by adding to 500 ml tetraethoxysilane, 290 ml of metal alkoxide solution prepared as described in Method 1. To this catalytic solution was added 15 grams (0.5 mole Si) silicon powder (95% Si:5% Fe+Mn, particle size 50-60 microns), i.e. 1580 ml catalytic solution/mole silicon, together with 60 ml dry ethanol. The procedure of example 1 was followed, giving a percentage conversion of silicon to tetraethoxysilane greater than 95% and a production rate of 35.7 grams/hour.

EXAMPLE 15

Following the procedure of example 1, silicon powder containing 0.5-1.5% Fe, 0.2-0.75% Ca and 0.5-1.5% Al was used. The catalytic solution was prepared by adding to 400 ml tetraethoxysilane, 200 ml of metal alkoxide solution prepared as described in Method 1. To this catalytic solution was added 16 grams (0.5 mole Si) of the silicon powder particle size 50-60 microns, i.e. 1200 ml catalytic solution/mole silicon, together with 30 ml dry ethanol. The average temperature of the reactor was 133° C. The reaction was carried out for 12 hours, 28.5 grams of the silicon and 360 ml dry ethanol being added. The percentage conversion of silicon to tetraethoxysilane was 66% and the production rate was 22 grams/hour.

EXAMPLE 16

A catalytic solution was prepared by adding 1000 ml tetraethoxysilane to 400 ml of metal alkoxide solution prepared according to Method 1. To this catalytic solution was added 28 g (1 mole) silicon, particle size 50–60 microns, i.e. 1400 ml catalytic solution/mole silicon, together with 70 ml dry ethanol. Following the procedure of example 1, 156.25 grams of silicon, particle size 5 microns or less were added together with 1920 ml dry ethanol in the course of 45½ hours. The reactor temperature was maintained at an average of 148° C. The percentage conversion of silicon to tetraethoxysilane was greater than 95% and the production rate was 53.5 grams/hour.

EXAMPLE 17

A catalytic solution was prepared by adding 600 ml tetraethoxysilane to 300 ml of metal alkoxide solution prepared according to Method 1. To this catalytic solution was added 28 grams (1 mole) silicon, particle size 50–60 microns, i.e. 900 ml catalytic solution/mole silicon together with 50 ml dry ethanol. Following the procedure of example 16, silicon of 74 micron particle size was used. The percentage conversion of silicon to tetraethoxysilane was greater than 95% and the production rate was 34 grams/hour.

EXAMPLE 18

A catalytic solution was prepared by adding 300 ml of tetraethoxysilane prepared as described in example 1 to 175 ml of the metal alkoxide product of Method 8. To this catalytic solution was added 14 grams (0.5 mole) silicon, particle size 50–60 microns, i.e. 950 ml catalytic solution/mole silicon together with 30 ml dry ethanol. Following the procedure of example 1, the reaction was carried out for 20½ hours, the mean reaction temperature being 158° C. 28 grams silicon and 230 ml dry ethanol were added. The percentage conversion of silicon to tetraethoxysilane was greater than 95% and the production rate was 10.2 grams/hour.

EXAMPLE 19

A catalytic solution was prepared by adding 340 ml of tetraethoxysilane prepared as described in example 1 to 170 ml of sodium 2-ethoxyethoxide solution prepared as described in Method 3. To this catalytic solution was added 14 grams (0.5 mole) silicon powder, particle size 50–60 microns, i.e. 1020 ml catalytic solution/mole silicon, together with 40 ml dry ethanol. Following the procedure of example 1, the reaction was carried out for 22½ hours, the mean reaction temperature being 148° C. 49 grams silicon and 290 ml ethanol were added. The percentage conversion of silicon to tetraethoxysilane was greater than 95% and the production rate was 15 grams/hour.

EXAMPLE 20

The procedure of example 19 was followed, except that the catalytic solution was prepared using 170 ml of potassium 2-ethoxyethoxide made as described in Method 3. The percentage conversion of silicon to tetraethoxysilane was greater than 95% and the production rate was 22 grams/hour.

EXAMPLE 21

A catalytic solution was prepared by adding 675 ml of tetraethoxysilane to 290 ml metal alkoxide solution prepared as described in Method 1. In this catalytic solution the volume ratio of solvent to metal alkoxide solution is 2.25:1. To the catalytic solution is added 14 g (0.5 mole) silicon, i.e. 1930 ml catalytic solution/mole silicon, together with 60 ml dry ethanol. The mixture was warmed to 145° C. and ethanol slowly added dropwise so as to maintain the reaction temperature in the range 165°–170° C. The tetraethoxysilane produced was removed from the reaction system by distillation as a mixture of ethanol and tetraethoxysilane. At 145° C. the production rate of tetraethoxysilane was 24 grams/hour. At the end of the reaction the production rate of tetraethoxysilane was 14.6 grams/hour.

EXAMPLE 22

In this example, the thermal capacity of the catalytic solution is first increased by stepwise additions of ethanol and silicon, then tetraethoxysilane and ethanol were removed as vapour and the sequence repeated.

STARTING PROCEDURE

A clean and dry reaction vessel is purged with dry nitrogen for about 15 minutes. The catalytic solution is made by charging the reaction vessel with 204 liters of tetraethoxysilane, followed by 204 liters of metal alkoxide solution prepared according to Method 4 and then by a further 136 liters of tetraethoxysilane. To this catalytic solution 5 kg silicon powder was added, i.e. 3046 ml catalytic solution/mole silicon, followed by 10 liters dry ethanol. The mixture was heated until the reactor temperature (pot temperature) was 140° C. At this stage the distillation head temperature (head temperature) was the ambient temperature

PRODUCTION OF TETRAETHOXYSILANE

Dry and pre-heated ethanol was added at a rate such that the pot temperature did not drop below 140° C. Ethanol was added at this required rate until evolution of hydrogen ceased. Then a further 5 kg silicon was added and more ethanol was added at the required rate until evolution of hydrogen ceased. No distillate was collected in this cycle, i.e. the reaction was done under total reflux condition.

It is necessary to maintain a minimum pot temperature of 140° C. Although a minimum pot temperature of 140° C. is required, the temperature is preferably in the range 155°–165° C. The ethanol addition can be replaced by a mixture of ethanol and tetraethoxysilane.

SEPARATION OF TETRAETHOXYSILANE FROM REACTION MIXTURE

The separation of tetraethoxysilane from the reaction mixture was carried out by the following procedure.

(i) The preferred pot temperature is 150° C.

(ii) Dry ethanol was added to the reaction mixture at a rate such that a constant head temperature is maintained.

(iii) It is preferable to remove the product as a mixture of tetraethoxysilane and ethanol. The product should be removed at a high head temperature (140° C. or over) to ensure that the distillate is rich in tetraethoxysilane. It is important that only the amount of tetraethoxysilane produced is removed.

The ethanol-tetraethoxysilane mixture collected is distilled to separate the ethanol and the tetraethoxysilane. The ethanol recovered can be re-used.

After the tetraethoxysilane produced has been removed, the sequence of stepwise additions of silicon and ethanol is repeated to continue the production of tetraethoxysilane. This in its turn is removed then the sequence of stepwise additions of silicon and ethanol is continued.

C - Preparation of ethyl polysilicate from tetraethoxysilane.

Tetraethoxysilane - 259 volumes
Anhydrous ethanol - 82.2 volumes
Water - 16.4 volumes - must be distilled or de-ionised
Acid solution - 1.3 volumes The acid solution is 1% v/v of concentrated sulphuric acid (98% $H_2SO_4$ by weight) in anhydrous ethanol.

The mixture of tetraethoxysilane, anhydrous ethanol and acid solution is heated to reflux temperature and water added dropwise with stirring over a period of 30 minutes. Refluxing is carried out for 60 minutes when the addition is completed. The ethanol is recovered from the product by distillation under gradual lowering of pressure. Distillation was finished when a pot temperature of 140° C. at 100 mm Hg pressure was reached. The amount of ethanol recovered was 180 volumes. This can be used again in the preparation.

Product characterisation
Density at 20° C.=1.06 gm/ml
Silica content=36.1% w/w
Acidity=0.013% wv $H_2SO_4$

GENERAL NOTES TO EXAMPLES

Moisture must be rigorously excluded. Reactions carried out in an atmosphere of dry nitrogen. Dry ethanol must be used, the procedures for drying are given in example 1. The rate of reaction may be followed by measuring the rate of hydrogen evolution. This is used to control the rate of addition of reactants to maintain optimum reaction rate. Usually silicon is added in batches and ethanol added dropwise, or a silicon/ethanol slurry added, when the observed rate of hydrogen evolution diminishes to a low value. The reaction temperature is maintained as constant as possible.

EXAMPLE 23

Preparation of sodium/potassium 2-ethoxyethoxide catalyst in the presence of toluene as diluent Reaction between sodium/potassium metals and 2-ethoxyethanol is shown below:

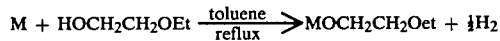

where, M=Na or K

REACTION PROCEDURE:

40–50 ml dry toluene were placed in a flask fitted with a reflux condenser, a nitrogen inlet, and a dropping funnel with the delivery end under the toluene and nitrogen inlet. Potassium (19 g; 0.5 mole) was introduced in the flask which was flushed thoroughly with dry nitrogen, then 2-ethoxyethanol was added slowly dropwise. All potassium dissolved after addition of 160 ml 2-ethoxyethanol. Then sodium (11.5 g; 0.5 mole) was introduced in the flask followed by the addition of 2-ethoxyethanol. The total volume of 2-ethoxyethanol added was 300 ml. The solution was gently warmed and the toluene then distilled off at 121° C.; while the remaining solution was refluxed for 4 hours until evolution of hydrogen ceased. The rate of addition of 2-ethoxyethanol is controlled by the rate of hydrogen evolution. The initial reaction between 2-ethoxyethanol and potassium is vigorous but soon subsides. The reaction with sodium is less vigorous. The 2-ethoxyethanol can be added to sodium and potassium metals. All reactions are carried out under dry nitrogen.

Unless otherwise stated, this procedure was used to prepare the sodium/potassium 2-ethoxyethoxide required in the following examples.

EXAMPLE 24

Preparation of ethyl silicate using sodium/potassium 2-ethoxyethoxide catalyst

Tetraethoxysilane was synthesised from dry ethanol and ferrosilicon using a sodium/potassium 2-ethoxyethoxide catalyst having a 1:1 molar ratio of sodium to potassium. Technical ethyl silicate was used to produce the catalytic solution. The rate of reaction, as measured by the rate of hydrogen evolution, was equivalent to producing 10 g/hour of tetraethoxysilane, and the reaction yield is greater than 95%.

1. REACTANTS

The silicon reactant used was initially a technical grade, a ferro-silicon. Later pure silicon was used, which affected the rate of reaction. The ethanol was 74 O.P.I.M.S. grade, which had been dried over sodium, and the solvent was technical ethyl silicate (40% w/w $SiO_2$). The catalyst was 1:1 molar ratio solution of sodium and potassium 2-ethoxyethodides prepared by dissolving sequentially 0.5 mole of sodium and 0.5 mole potassium in 2-ethoxyethanol (4 mole, 350 ml). This was carried out under a nitrogen blanket. The above solution was refluxed for a minimum of 1.5 hours, then cooled to ambient temperature. The preferred time of refluxing is 4 hours. 500 ml of technical ethyl silicate were added to produce the catalytic solution. The initial concentration of reactants is given in Table A. During the course of the reaction, a further 6 g of technical silicon and 65.5 g of pure silicon were added, together with 462 ml of dry ethanol.

2. CONDITIONS

The initial temperature at which hydrogen was evolved was 110° C. and during the course of the reaction the reactor temperature varied between 115° C. and 180° C., the usual temperature being 150°±10° C. The head temperature varied between 78° and 126° C. when product was being collected. It was found that the reactor temperature could be controlled by the rates of addition of ethanol and removal of product. The reaction was run for a total of 50 hours over a seven day period.

3. REACTION RATE AND PRODUCT YIELD

The rate of reaction as measured by the rate of hydrogen evolution is given in Table A. During the first three days, when ferrosilicon was used, the hydrogen evolution rate was consistently between 40 and 50 ml per minute. Based on this figure, the yield is greater than 95% and the production rate of tetraethoxysilane is 10 g/hour.

There was a material balance at the end of the reaction.

Table A sets out the reaction details:

TABLE A

| Materials Used | Initially | Total |
|---|---|---|
| 1. Silicon | 29 g | 101.5 g |
| 2. Dry Ethanol | 50 ml | 512 ml |
| 3. Technical Ethyl Silicate | 500 ml | 500 ml |
| 4. Sodium/potassium 2-ethoxyethoxide (sodium and potassium are in the molar ratio of 1 : 1) | 350 ml | 350 ml |
| 5. Total Used | | 1582 ml |
| 6. Total Collected | | 1585 ml |
| Temperatures | | |
| 1. Initial reactor temp. when hydrogen evolved | | 110° C. |
| 2. Range of reactor temp. | | 115° C.–180° C. |
| 3. Range of Head temp. | | 78° C.–126° C. |
| Rate of Reaction | | |

| Day | 1 | 2 | 3 | 4[1] | 5 | 6[2] | 7 |
|---|---|---|---|---|---|---|---|
| Rate of Hydrogen evolution (cm$^3$/min) | 40 | 50 | 40 | 75 | 140 | 190 | 9 |

[1] Pure silicon used from day 4 onwards
[2] Leak in the system inflated figures. Effect on average rate of hydrogen evolution by adding:
Silicon - None
Ethanol - None
2-Ethoxyethanol - None

EXAMPLE 25

Potassium 2-ethoxyethoxide was prepared by dissolving potassium (19.0 g; 0.5 mole) in 2-ethoxyethanol (180 g; 2 mole) under nitrogen at room temperature. Similarly, sodium 2-ethoxyethoxide is prepared by dissolving sodium (11.5 g; 0.5 mole) in 2-ethoxyethanol (180 g; 2 mole).

Sodium and potassium 2-ethoxyethoxides prepared as above were then combined with a solution containing technical ethyl silicate (40% SiO$_2$) (500 ml), freshly distilled ethanol (303.5 g; 6.6 mole) and dry silicon powder (12 g) in a 2 liter three-neck flask fitted with partial take-off head, mechanical stirrer, dropping funnel, thermometer and nitrogen inlet. The solution was gradually heated (70°–80° C.) for ~3 hours using an isomantle. Unreacted ethanol nd 2-ethoxyethanol was then distilled off at a reactor temperature of ~120° C. After collection of ~580 ml distillate (b.p. 82°–90° C.), the reactor temperature increased to 145° C. and hydrogen was evolved. At this stage a slurry of silicon in dry ethanol (1:4 mole ratio) was added to the reaction mixture. The reactor temperature rose immediately and was carefully maintained in the range of 165°–190° C. by adjusting the rate of addition of siliconethanol slurry. The distillate (b.p. 115°–130° C.) collected at the rate of ~90 ml/hour. The reaction was carried out for 40 hours, during which time ~3500 ml distillate collected. This was further fractionated using a Vigreux column at atmospheric pressure and gave ~750 g pure tetraethoxysilane (b.p. 168°–170° C.), confirmed by IR spectrum. Recovered ethanol is recycled.

EXAMPLE 26

Potassium ethoxide was prepared by slowly adding potassium (5.5 g; 0.14 mole) to a solution containing technical ethylsilicate (40% SiO$_2$) (110 ml) and freshly distilled ethanol (46 g; 1 mole). In the same solution sodium ethoxide was prepared by dissolving sodium (3.2 g; 0.14 mole). Finally silicon powder (6 g) was added and the mixture was refluxed for about 3 hours. Excess ethanol was distilled off to increase the reactor temperature to 145° C. when hydrogen evolution commenced. A slurry of silicon in ethanol (1:4 molar ratio) was gradually added, the reactor temperature rose immediately to 165° C. and the rate of hydrogen evolution increased. By adjusting the rate of addition of siliconethanol slurry, the reactor temperature was carefully maintained in the range of 165°–180° C. The reaction was carried out for 6 hours during which time a total of 225 ml of distillate (b.p. 130°–156° C.) was collected. This, on further fractionation at atmospheric pressure gave 125 g pure tetraethoxysilane (b.p. 168°–170° C.) confirmed by IR spectrum. The recovered ethanol was recycled.

EXAMPLE 27

Preparation of tetraethoxysilane using sodium/potassium 2-ethoxyethoxide (1:1 molar ratio) and tetraethoxysilane as catalytic solution Preparation of catalyst Potassium (19 g; 0.5 mole) was slowly added to 2-ethoxyethanol (290 ml) in a flask fitted with a reflux condenser and nitrogen inlet. The flask and contents was warmed gently for 3 hours and sodium then added (11.5 g; 0.5 mole). The mixture was refluxed slowly for a period of about 4 hours until evolution of hydrogen ceased.

The initial solution was pale yellow but turned wine red after 2 hours and became very viscous on cooling to room temperature.

All reactions were carried out under nitrogen.

14 g (0.5 mole) of ferrosilicon was placed in a 2 l reaction flask which had been thoroughly flushed with nitrogen and fitted with a reflux condenser, distillation head, thermometer, dropping funnel, stirrer and isomantle.

500 ml of pure tetraethoxysilane were added to the sodium/potassium 2-ethoxyethoxide solution to obtain the catalytic solution. This solution was placed in the reaction flask, then 60 ml (~1 mole) ethanol were added and the mixture gently warmed.

Slow evolution of hydrogen was observed at room temperature which gradually increased as the reaction temperature rose. Details are shown in Table B.

During the reaction, ethanol was added dropwise to maintain a steady evolution of hydrogen. However, addition of ethanol was discontinued from time to time in order to maintain a steady reaction temperature. When hydrogen evolution ceased, a further 14 g (0.5 mole) of ferrosilicon was added then the dropwise addition of ethanol was continued.

The reaction product was collected from the second day onwards. The results are given in Table B.

TABLE B

Preparation of Tetraethoxysilane Using Sodium Potassium 2-Ethoxylthoxide as Catalyst and Tetraethoxysilane as Catalytic Solution

| | | |
|---|---|---|
| 1. | Total moles of catalyst used | 1 |
| 2. | Molar ratio of sodium and potassium in the catalyst | 1:1 |
| 3. | Initial weight of ferrosilicon used | 14 g (0.5 mole) |
| 4. | Volume of pure tetraethoxysilane used | 500 ml |
| 5. | Initial volume of ethanol used | 60 ml |
| 6. | Initial reaction tempera- | |

TABLE B-continued

Preparation of Tetraethoxysilane Using Sodium Potassium 2-Ethoxylthoxide as Catalyst and Tetraethoxysilane as Catalytic Solution

| | | |
|---|---|---|
| | ture (i.e. the temperature when hydrogen evolution was first observed | 25° C. |
| 7. | Maximum reaction temperature attained | 186° C. |
| 8. | Distillation head temperature attained | |
| | min$^m$ | 25° C. |
| | max$^m$ | 150° C. |
| 9. | Average rate of hydrogen evolution | |
| | 1st batch | 86 ml/min |
| | 2nd batch | 147 ml/min |
| | 3rd batch | 183 ml/min |
| | 4th batch | 146 ml/min |
| | 5th batch | 92 ml/min |
| | 6th batch | 122 ml/min |
| | 7th batch | 92 ml/min |
| 10. | Yield of TES wrt ferrosilicon powder | >90% |
| 11. | Effect of adding ferrosilicon during reaction | Rate of hydrogen evolution increases |
| 12. | Effect of adding ethanol during the reaction | Rate of hydrogen evolution and head temp. increases; reaction temp. decreases |
| 13. | Effect of increasing reaction temperature | Reaction rate in general increases; however temp. higher than 190° C. may have detrimental effect on catalyst and/or product. |
| 14. | Nature of product | |
| | Initial | mixed |
| | Final | pure Si(OEt)$_4$ |
| 15. | Activity of reaction mixture at the end of trial period | Unchanged |
| 16. | Total amount of ferrosilicon added | 112 g (4 moles) |
| 17. | Total moles of ethanol added | 1000 ml (17.25 moles) |

EXAMPLE 28

7 g of technical silicon powder were placed in a 2 l reaction flask fitted with a reflux condenser, distillation head, thermometer, dropping funnel, stirrer and electric heating jacket. The flask is thoroughly flushed with dry nitrogen.

250 ml of polymethylphenylsiloxane (commercially sold as Dow Corning 550 fluid by Dow Corning U.K.) were mixed with 150 ml of sodium/potassium 2-ethoxyethoxide catalyst solution prepared as previously described (sodium and potassium are in the molar ratio of 1:1) which was placed in the flask. Finally 30 ml of dry ethanol were added and the solution warmed gently.

Slow evolution of hydrogen was observed at ambient temprature. The hydrogen evolution gradually increased as the temperature rose. During the reaction, a temperature in the range of 90°-130° C. is maintained.

Progress of the reaction was monitored by measuring the rate of hydrogen evolution. Drops of ethanol were added to maintain a steady flow of hydrogen. However addition of ethanol was discontinued from time to time in order to maintain a steady reaction temperature.

Hydrogen evolution varied from 40 ml/min to a maximum of 200 ml/min which corresponded to a tetraethoxysilane yield of ~11 g/hour and 56 g/hour respectively.

A fresh batch of 7 g of technical silicon powder was added when the hydrogen evolution slowed down to a steady rate of 40 ml/min.

A mixture of ethanol and product tetraethoxysilane was slowly distilled off during the reaction. It is further fractionated at atmospheric pressure to obtain pure tetraethoxysilane (b.p. 162°-168° C./760 mmHg). The purity of the product was demonstrated by IR analysis.

The reaction was carried out for a total period of 10 hours.

EXAMPLE 29

7 g of technical silicon powder was placed in a 2 l reaction flask fitted with a reflux condenser, distillation head, thermometer, dropping funnel, stirrer and electric heating jacket. The flask was thoroughly flushed with dry nitrogen. A catalytic solution comprising a mixture of 125 ml polymethylphenylsiloxane (commercially sold as Dow Corning 550 fluid by Dow Corning U.K.), 125 ml pure tetraethoxysilane and 150 ml of a solution of sodium/potassium 2-ethoxyethoxide prepared as previously described (sodium and potassium are in the molar ratio of 1:1) was prepared and placed in the flask. Finally 30 ml of dry ethanol were added and the mixture warmed gently.

Slow evolution of hydrogen was observed at ambient temperature; it gradually increased with increase in temperature. During the reaction, a temperature in the range of 90°-130° C. is maintained.

Progress of the reaction was monitored by measuring the rate of hydrogen evolution. Drops of ethanol were added to maintain a steady flow of hydrogen. However, addition of ethanol was discontinued from time to time in order to maintain a steady reaction temperature.

Hydrogen evolution varied from 40 ml/min to a maximum of 400 ml/min which corresponded to a tetraethoxysilane yield of ~11 g/hour and 112 g/hour respectively. A fresh batch of 7 g of technical silicon powder was added when the hydrogen evolution slowed down to a steady rate of 40 ml/min.

A mixture of ethanol and product tetraethoxysilane was slowly distilled off during the reaction. It was further fractionated at atmospheric pressure to obtain pure tetraethoxysilane (b.p. 162°-168° C./760 mmHg). The purity of the product was demonstrated by IR analysis.

The reaction was carried out for a total period of 8 hours.

EXAMPLE 30

Stage A

Potassium metal (19 g; 0.5 mole) was slowly added to 290 ml (2.0 mole) 2-ethoxyethanol in a flask fitted with a reflux condenser and nitrogen inlet. The solution was warmed gently for 3 hours then sodium metal (11.5 g; 0.5 mole) was added and the resultant solution refluxed for 4 hours.

Stage B 15 grams (0.5 mole) of silicon (95%, Si 5% Fe+Mn) were placed in a 2 l flask fitted with reflux condenser and distillation head, thermometer, dropping funnel, stirrer and nitrogen inlet. An electric heating jacket was used to heat the flask and contents. The flask was purged with nitrogen. To the product from Stage A, 500 ml (2.24 mole) tetraethoxysilane were added to make the catalytic solution. The solution was added to the reaction flask, followed by 60 ml (1 mole) of ethanol and warmed. Silicon carbide passing 200 mesh B.S. 410 sieve can be used instead of silicon.

Stage C

Ethanol was added dropwise. Hydrogen was evolved slowly at ambient temperature. The evolution rate increased rapidly as the temperature rose. During the reaction, the temperature of the reaction system should not fall below 130° C., the rate of addition of ethanol being adjusted to keep the reaction temperature above 130° C. The amount of ethanol added was 125 ml (2 moles). The preferred range of reaction temperature is 145°–175° C.

Stage D

When 22 liters of hydrogen were evolved, 15 grams (0.5 mole) of silicon (95%, Si, 5% Fe+Mn) were added followed by 125 ml (2 moles) of ethanol dropwise as in Stage C. The tetraethoxysilane formed was removed as a tetraethoxysilane ethanol mixture. Fractional distillation of this mixture gave pure tetraethoxysilane as demonstrated by IR analysis. When a further 22 liters of hydrogen had evolved, Stage D was repeated. The results are given in Table C.

Unless otherwise stated, all liquid reagents and solvents were dried by treatment with molecular sieves and dry nitrogen was used.

TABLE C

| Batch No. | Rate of production of tetraethoxy-silane (moles/hour) | Temperatures °C. | | | | Remarks |
|---|---|---|---|---|---|---|
| | | Reaction | | Distillation head | | |
| | | min. | max. | min. | max. | |
| 1 | 0.12 | 100 | 130 | 25 | 80 | No Si(OEt)$_4$ removed |
| 2 | 0.20 | 130 | 160 | 60 | 82 | |
| 3 | 0.25 | ambient | 162 | 66 | 112 | Reaction system closed down overnight |
| 4 | 0.20 | 148 | 165 | 45 | 86 | |
| 5 | 0.13 | ambient | 160 | ambient | 73 | Reaction system closed down overnight |
| 6 | 0.17 | 140 | 162 | 73 | 85 | |
| 7 | 0.13 | ambient | 188 | 72 | 150 | Reaction system closed down overnight. Product removed rich in Si(OEt)$_4$ and poor in ethanol. |

Stage A-Alternative procedure

40–50 ml of dry toluene were added to a flask fitted with a reflux condenser, dropping funnel and nitrogen inlet. 19 g (0.5 mole) of potassium metal were introduced in the flask which was flushed with dry nitrogen and then slowly and dropwise were added 160 ml of 2-ethoxyethanol. Sodium metal (11.5 g; 0.5 mole) was added followed by 140 ml of 2-ethoxyethanol added slowly dropwise. The solution was warmed gently and the toluene distilled off at atmospheric pressure; then the solution was refluxed for 4 hours. It is desirable but not necessary to distill off the toluene. A dry nitrogen atmosphere must be maintained throughout the preparation.

EXAMPLE 31

Preparation of ethyl polysilicate from tetraethoxysilane

Tetraethoxysilane-259 volumes
Anhydrous ethanol-82.2 volumes
Water-16.4 volumes must be distilled or de-ionised
Acid solution-1.3

The acid solution is 1% v/v of concentrated sulphuric acid (98% H$_2$SO$_4$ by weight) in anhydrous ethanol.

The mixture of tetraethoxysilane, anhydrous ethanol and acid solution is heated to reflux temperature and water added dropwise with stirring, over a period of 30 minutes. Refluxing is carried out for 60 minutes when the addition is completed. The ethanol is recovered from the product by distillation under gradual lowering of pressure. Distillation is finished when a reactor temperature of 140° C. at 100 mm Hg. pressure is reached. The amount of ethanol recovered is 180 volumes. This can be used again in the preparation.

PRODUCT CHARACTERISATION

Density at 20° C.=1.06 gm/ml
Silica content=36.1% w/w
Acidity=0.013 w/v H$_2$SO$_4$.

EXAMPLE 32

Industrial application-preparation of tetraethoxysilane by semi-batch process

The thermal capacity of the catalytic solution is first increased by stepwise additions of ethanol and silicon, then tetraethoxysilane and ethanol are removed as vapour and the sequence repeated.

STARTING PROCEDURE

A clean and dry reaction vessel is purged with dry nitrogen for about 15 minutes. The catalytic solution is made by charging to the reaction vessel 45 gallons of tetraethoxysilane, followed by 45 gallons of sodium/-potassium 2-ethoxyethoxide (1:1 molar ratio of sodium to potassium) prepared by the procedure previously described, then by a further 30 gallons of tetraethoxysilane. To this catalytic solution, 5 kg silicon powder and 10 liters of ethanol were added. The mixture was heated until the reactor temperature rose to 140° C. At this stage the distillation head temperature was at ambient temperature.

PRODUCTION OF TETRAETHOXYSILANE

Dry and pre-heated ethanol was added at a rate such that the reactor temperature does not drop below 140° C. Ethanol was added at the required rate until evolution of hydrogen ceases. Then a further 5 kg of silicon was added together with more ethanol at the required rate until the evolution of hydrogen ceased. No distillate was collected in this cycle, i.e. reaction is run under total reflux condition. Stepwise addition of silicon and ethanol was continued until 50 kg of silicon had been added.

NOTES (a) It is necessary to maintain a minimum reactor temperature of 140° C.

(b) Although a minimum reactor temperature of 140° C. is required, the temperature is preferably in the range of 155°–165° C.

(c) The ethanol addition can be replaced by the addition of a mixture of ethanol and tetraethoxysilane.

(d) Only 5 kg of silicon powder should be added at a time.

SEPARATION OF TETRAETHOXYSILANE FROM THE REACTION MIXTURE

The separation of tetraethoxysilane from the reaction mixture has been successfully carried out by the following procedure:

(i) Minimum reactor temperature desirable is 150° C.

(ii) Dry ethanol is added to the reaction mixture at a rate such that a constant head temperature is maintained.

(iii) It is preferable to remove the product (as a mixture of ethanol and tetraethoxysilane) at a high head temperature (140° C. or over) to ensure that the distillate is rich in tetraethoxysilane.

(iv) It is important that only the amount of tetraethoxysilane produced during the run is removed.

The ethanol-tetraethoxysilane mixture collected is fractionally distilled to separate the ethanol and the tetraethoxysilane. The ethanol recovered can be re-used.

After the tetraethoxysilane produced has been removed from the reactor, the sequence of stepwise additions of silicon and ethanol is repeated to continue the production of tetraethoxysilane. This in turn is removed and the sequence of stepwise additions of silicon and ethanol is continued.

We claim:

1. A method of manufacturing tetraalkoxysilane comprising the steps of:
   preparing a reaction mixture comprising a catalytic solution, a silicon or silicide, and an alkanol,
   maintaining a high thermal capacity in said reaction mixture by maintaining a large volume of catalytic solution relative to the silicon or silicide present in said reaction mixture,
   raising the temperature of said reaction mixture and maintaining the temperature of said reaction mixture at a level effective to discharge tetraalkoxysilane as a vapour together with alkanol vapour and hydrogen gas.

2. A method of manufacturing tetraethoxysilane comprising the steps of:
   preparing a reaction mixture comprising a catalytic solution, a silicon or silicide, and ethanol,
   maintaining a high thermal capacity in said reaction mixture by maintaining a large volume of catalytic solution relative to the silicon or silicide present in said reaction mixture,
   raising the temperature of said reaction mixture and maintaining the temperature of said reaction mixture at a level effective to discharge tetraethoxysilane as a vapour together with ethanol vapour and hydrogen gas.

3. The method of claim 2 wherein said reaction mixture contains at least 500 milliliters of said solution for each mol of silicon or silicide present in said solution.

4. A method as claimed in claim 3 wherein the thermal capacity is maintained or increased by additions of silicon or a silicide, the vapours and gas being removed and the sequence repeated.

5. A method as claimed in claim 3 wherein the reaction temperature is maintained within the range 135° to 170° C.

6. A method as claimed in claim 5 wherein the reaction temperature is maintained within the range 150° to 165° C.

7. A method as claimed in claim 3 wherein there is not more than 3000 ml of catalytic solution for each mole of silicon.

8. A method as claimed in claim 3 wherein the catalytic solution contains a liquid catalyst capable of forming a complex with the reagents and thereafter disassociating thereby regenerating the catalyst and the reaction product, and a high boiling point chemically inert solvent liquid.

9. A method as claimed in claim 8 wherein the solvent has the following general formula:

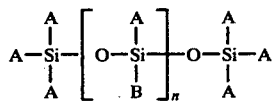

10. A method as claimed in claim 8 wherein the solvent has the following general formula:

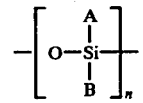

where n is 3 or a whole number greater than 3.

11. A method as claimed in claim 8 wherein the catalyst is a metal alkoxide.

12. A method as claimed in claim 11 wherein the catalyst is the alkoxide prepared by successively adding sodium and potassium to the alcohol.

13. A method as claimed in claim 12 wherein the alkoxide is formed by adding sodium and potassium successively to a glycol.

14. A method as claimed in claim 11 wherein the volume ratio of solvent to alkoxide has a value of between 2.25:1 and 0.5:1.

15. A method as claimed in claim 11 wherein the catalytic solution is prepared by the following steps:

(1) Dissolving a metal or metals in an alcohol under an inert atmosphere, for example nitrogen;

(2) Warming the solution produced in (1) preferably under reflux;

(3) Adding to the metal alkoxide catalyst produced a relatively large volume of high boiling point inert and neutral solvent;

(4) Adding to the catalytic solution silicon or a silicide in admixture with liquid dry ethanol;

(5) Warming the solution preferably to at least 110° C. to initiate the catalysed reaction; and (6) Adding further dry liquid ethanol.

16. A method as claimed in claim 15 wherein steps (4) to (6) are modified by adding the silicon or silicide to the solution of (3) subsequently warming and thereafter adding the ethanol.

17. A method as claimed in claim 3 wherein the rate of reaction is monitored by measuring the rate of hydrogen evolution.

18. A method as claimed in claim 3 wherein the alkyl silicate reaction product is to yield ethyl polysilicate.

19. A method as claimed in claim 18 wherein the polymerisation is effected by digestion with alcohol in an aqueous acidic solution thereby effecting hydrolysis and condensation/polymerisation.

20. A method according to claim 1 or 2 wherein the silicon or silicide is silicon carbide.

* * * * *